United States Patent
Kikta

(10) Patent No.: US 7,556,769 B2
(45) Date of Patent: Jul. 7, 2009

(54) FECAL OCCULT TEST PACKAGING

(76) Inventor: Kevin Kikta, 12 Crowel Rd., Hillsborough, NJ (US) 08844

( * ) Notice: Subject to any disclaimer, the term of this patent is extended or adjusted under 35 U.S.C. 154(b) by 414 days.

(21) Appl. No.: 11/558,882

(22) Filed: Nov. 10, 2006

(65) Prior Publication Data
US 2008/0113427 A1 May 15, 2008

(51) Int. Cl.
G01N 33/72 (2006.01)
G01N 31/22 (2006.01)
G01N 21/03 (2006.01)
G01N 21/77 (2006.01)

(52) U.S. Cl. .............. 422/58; 422/55; 422/56; 422/61; 422/99; 436/63; 436/66; 436/164; 436/165; 436/169; 436/170; 206/459.1; 206/569; 435/287.1; 435/287.6

(58) Field of Classification Search .......... 436/63, 436/66, 164, 165, 169, 170; 422/55, 56, 422/58, 60, 61, 99, 102; 206/459.1, 569; 435/287.1, 287.6
See application file for complete search history.

(56) References Cited

U.S. PATENT DOCUMENTS

| | | | | | |
|---|---|---|---|---|---|
| 3,996,006 | A | * | 12/1976 | Pagano | 422/50 |
| 4,225,557 | A | * | 9/1980 | Hartl et al. | 422/56 |
| 4,365,970 | A | * | 12/1982 | Lawrence et al. | 436/66 |
| 4,511,533 | A | * | 4/1985 | Guadagno et al. | 422/61 |
| 4,562,043 | A | * | 12/1985 | Mennen et al. | 422/56 |
| 4,582,685 | A | * | 4/1986 | Guadagno et al. | 422/61 |
| 4,645,743 | A | * | 2/1987 | Baker et al. | 436/66 |
| 4,647,541 | A | * | 3/1987 | Guadagno et al. | 436/66 |
| 4,789,629 | A | * | 12/1988 | Baker et al. | 435/7.92 |
| 4,983,416 | A | * | 1/1991 | Hunsinger et al. | 427/2.13 |
| 5,100,619 | A | * | 3/1992 | Baker et al. | 422/58 |
| 5,182,191 | A | * | 1/1993 | Fan et al. | 435/7.9 |
| 5,264,181 | A | * | 11/1993 | Schreiber | 422/58 |
| 5,391,498 | A | | 2/1995 | Baker | |
| 5,840,584 | A | * | 11/1998 | Waldenburg | 436/66 |
| 6,077,711 | A | * | 6/2000 | Singer | 436/66 |
| 6,436,714 | B1 | | 8/2002 | Clawson | |
| 7,189,356 | B1 | * | 3/2007 | Clawson | 422/56 |
| 2005/0164397 | A1 | * | 7/2005 | Waldenburg | 436/66 |
| 2006/0018789 | A1 | | 1/2006 | Lastella | |
| 2008/0131971 | A1 | * | 6/2008 | Clawson | 436/66 |

OTHER PUBLICATIONS

Hemaprompt website http://www.hemaprompt.com (copy attached, printed from website Feb. 6, 2008.

* cited by examiner

*Primary Examiner*—Maureen M Wallenhorst
(74) *Attorney, Agent, or Firm*—Jennifer Meredith, Esq

(57) ABSTRACT

A specimen testing device having a folding top having a top inside and a top outside; a back portion having at least one flap opening, the back portion in folding communication with the folding top; a front portion having at least one opening with the folding top covering the front portion when in a folded closed position and the front portion in folding communication with the back portion; a reagent test sheet in communication with at least a portion of the back portion and interposed between the front portion and the back portion; at least one enclosed bubble containing developer attached to the inside of the flap opening of the back portion, wherein a fecal sample is placed on the reagent test sheet, the folding top is in a folded closed position and the enclosed bubble releases the developer to indicate the presence of fecal occult blood.

19 Claims, 4 Drawing Sheets

FECAL OCCULT TEST PACKAGING

The present invention relates to packaging for the handling and detection of fecal occult blood.

It is well know that colorectal cancer and large polyps bleed into the stool. Fecal occult blood may provide a reliable diagnostic indicator of a variety of medical conditions involving gastrointestinal bleeding which may otherwise be difficult to detect, including colorectal cancer. The use of this method is well described in the medical literature. See e.g., Greegor, D. H., Cancer 19; 330-337 (1969) and Hastings, J. B., Amer. J. Surg. 127:228-233 (1974). Tests for fecal occult blood based upon the oxidation of guaiac to form a blue colored product in the presence of hydrogen peroxide and hemoglobin have been described in U.S. Such products are sold under the trademarks HEMOCCULT® and SERAC-ULT®. Briefly, the test involves placing a fecal sample on an absorbent paper coated with guaiac and adding a developer solution containing hydrogen peroxide. If hemoglobin is present, the guaiac is oxidized, turning the paper blue. Another test involved the use of a paper coated with o-tolidine and a developer of peroxide. Different reagents may be used as they provide different levels of sensitivity to avoid false positives.

The problem with these products is that there may be numerous folding slides around an office, but only one or two bottles of developer. This can cause many problems including not being able to locate the single bottle of developer, contamination from numerous people touching the bottle and finally that physicians may want to give a slides to a patient for self testing, but can't give each of them an entire bottle of developer as they may only have a single bottle. Also, if the physician or nurse wants to use two different solutions to test the patients slide, they must separately find and open two bottles and drop the solutions on the slide. This is time consuming.

Accordingly, the present invention provides a self contained device that does not require a separate bottle of developer and may provide separate bubbles each containing different developers.

SUMMARY OF THE INVENTION

The present invention relates generally to devices for evaluating the presence of fecal occult blood.

According to one embodiment, a specimen testing device is disclosed comprising: a folding top having a top inside and a top outside; a back portion having at least one flap opening in communication with the folding top; a front portion having at least one opening with the folding top covering the front portion and the front portion in communication with the back portion; a reagent test sheet affixed to the back portion the reagent test sheet interposed between the front portion and the back portion; at least one enclosed bubble containing developer attached to the inside of the flap opening of the back portion.

According to another embodiment, a specimen testing device is disclosed, comprising: a folding top having a top inside having a raised portion and a top outside; a back portion having at least one flap opening in folding communication with the folding top; a front portion having at least one opening with said folding flap covering the front portion and the front portion in folding communication with the back portion; a reagent test sheet affixed to the back portion the reagent test sheet interposed between the front portion and the aid back portion; an enclosed bubble containing developer attached to the inside of the flap opening of the back portion, wherein the enclosed bubble is burst when the folding top is closed and pressure is placed.

These and other features, aspects and advantages of the present invention will become better understood with reference to the following description and claims.

DETAILED DESRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Figure 1:
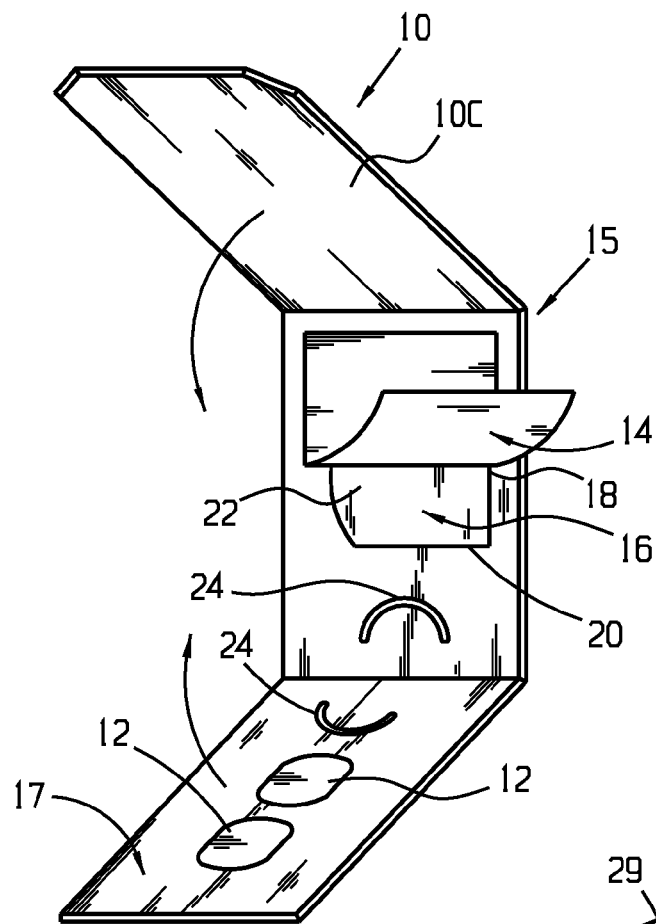
FIG. 1 depicts the present invention.
Figure 2:
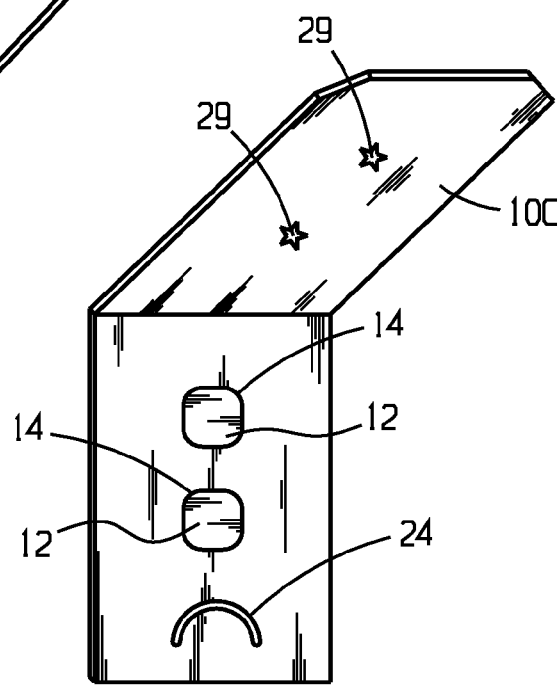
FIG. 2 depicts the present invention.
Figure 3:
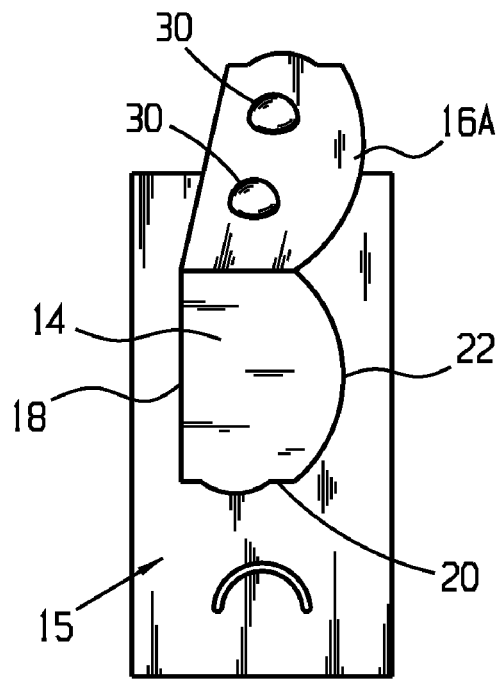
FIG. 3 depicts the present invention.
Figure 4:
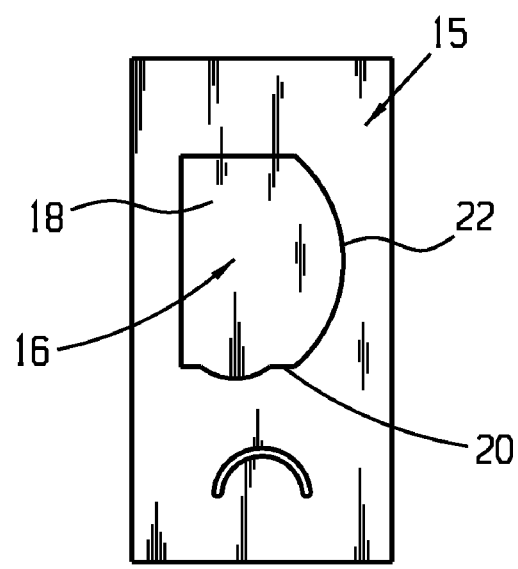
FIG. 4 depicts the present invention.
Figure 5:
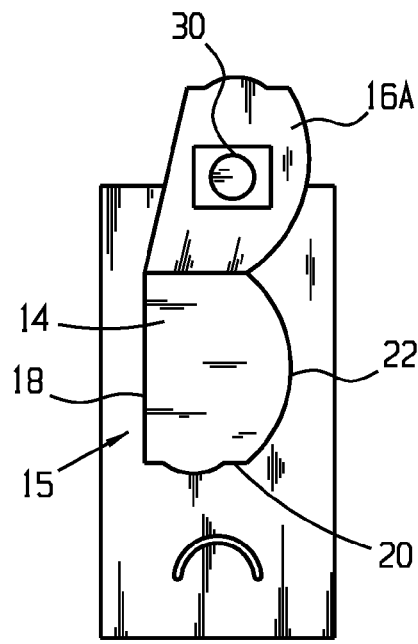
FIG. 5 depicts the present invention.
Figure 6:
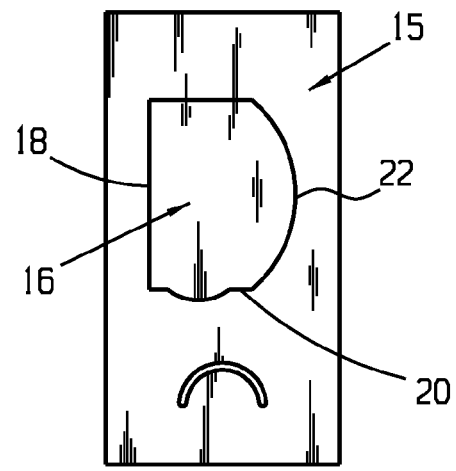
FIG. 6 depicts the present invention.
Figure 7:
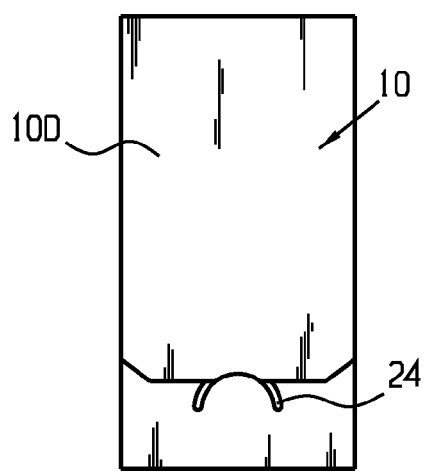
FIG. 7 depicts the present invention.
Figure 8:
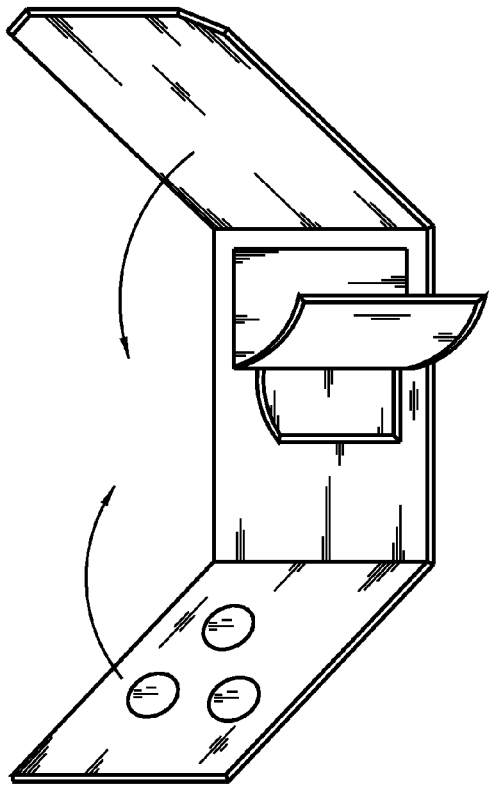
FIG. 8 depicts the present invention.
Figure 9:
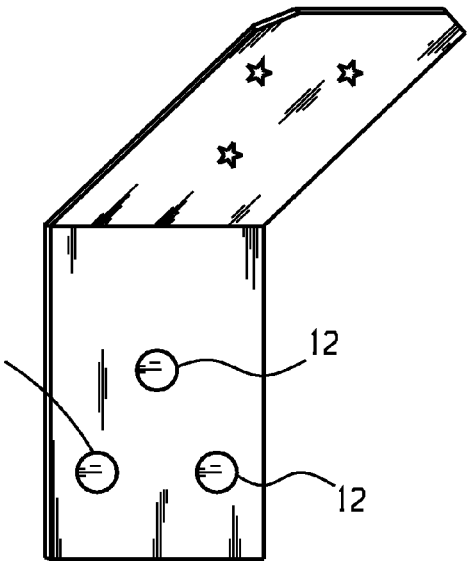
FIG. 9 depicts the present invention.
Figure 10:
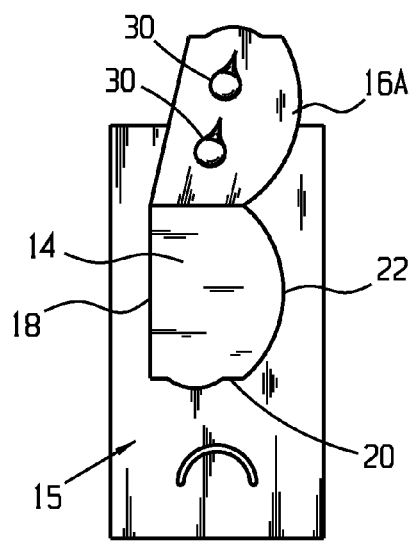
FIG. 10 depicts the present invention.

As shown in FIGS. 1-9, the present invention provides a specimen testing device (10) having a folding top (10) having a top inside (10*c*) and a top outside (10*d*); a back portion (15) having at least one flap opening (22). The back portion (15) may be in folding communication with the folding top (10). The front portion (17) having at least one opening (12) with the folding top (10) covering the front portion (17) and the front portion (17) may be in folding communication with the back portion (15). A reagent test sheet (14) may be affixed to the back portion (15) with the reagent test sheet (14) interposed between the front portion (17) and the back portion (15). An enclosed bubble (30) containing developer may be attached to the inside (16*a*) of the flap opening (16) of the back portion (15). It should be understood that the opening of the back portion (15) does not need to be a flap opening (16). However, this is useful, as the enclosed bubble (30) may be kept in an open position to avoid the enclosed bubble (30) from inadvertently releasing the developer. There may also be a raised portion on the top inside (10*c*) directly opposing the enclosed bubble (30) when the folding top is in a closed position. It should be understood the raised portion (29) is separated from the enclosed bubble by the reagent test sheet (14). The raised portion (29) may be sharp and/or pointed. The developer may be a stabilized aqueous solution of 5% hydrogen peroxide and 75% ethanol. It may be any other developer known within the art. There may be more than one enclosed bubble (30) and each enclosed bubble (30) may contain a different developer. This is particularly desirable as different developers may provide different levels of accuracy. The at least one opening (12) of the front portion (17) is two aligned round openings (as shown in FIGS. 1-2). There may be a hydrophobic barrier between the two aligned round openings. The at least one opening (12) of the front portion (17) may also be three openings (12) forming a triangular shape (as shown in FIGS. 8-9). There may also be a hydrophobic barrier surrounding the at least one flap opening of the back portion. There may also be an indicator such as a plus sign (as shown in FIG. 2) printed on the reagent test strip (14) in the center of the at least one opening (12). A fecal sample may be placed on the indicator and the folding top (10) closed. Pressure may then be placed on the middle of the specimen testing device, bursting the enclosed bubble (30), releasing the developer to indicate the presence of fecal occult blood. As depicted in FIG. 10, the bubble (30) may be tear drop shaped or any similar shape with a tail directing the fluid to a particular spot.

It should be understood that the foregoing relates to preferred embodiments of the invention and that modifications may be made without departing from the spirit and scope of the invention as set forth in the following claims.

I claim:

1. A specimen testing device, comprising:
    a folding top having a top inside and a top outside;
    a back portion having a back inside, a back outside and at least one flap opening, said back portion in folding communication with said folding top;
    a front portion having at least one opening, wherein said front portion is in folding communication with said back portion and said folding top covers said front portion when said front portion is in a folded closed position;
    a reagent test sheet in communication with at least a portion of said back portion and interposed between said front portion and said back portion when said front portion is folded over said back portion; and
    at least one enclosed bubble containing developer attached to the inside of said flap opening of said back portion,
    wherein a fecal sample is placed on said reagent test sheet in each said at least one opening of said front portion when said front portion is folded over said back portion, said folding top is folded into a folded closed position and wherein each said at least one enclosed bubble is burst when pressure is placed on said folding top in said folded closed position and said at least one enclosed bubble releases said developer to the fecal sample to indicate the presence of fecal occult blood.

2. A specimen testing device as in claim 1, wherein said top inside has a raised portion directly opposing said at least one enclosed bubble when said folding top is in a closed position.

3. A specimen testing device as in claim 1, wherein said developer is a stabilized aqueous solution of hydrogen peroxide and ethanol.

4. A specimen testing device as in claim 1, wherein each said at least one enclosed bubble contains a different developer.

5. A specimen testing device as in claim 1, wherein said at least one opening of said front portion is two aligned round openings.

6. A specimen testing device as in claim 1, wherein said at least one opening in said front portion is two aligned round openings and further comprising a hydrophobic barrier between said two aligned round openings.

7. A specimen testing device as in claim 1, wherein said at least one opening of said front portion is three openings forming a triangular shape.

8. A specimen testing device as in claim 1, further comprising a hydrophobic barrier surrounding said at least one flap opening of said back portion.

9. A specimen testing device as in claim 1, further comprising an indicator printed on said reagent test sheet in the center of said at least one opening.

10. A specimen testing device as in claim 1, wherein said at least one bubble is tear drop shaped.

11. A specimen testing device, comprising:
    a folding top having a top inside having a raised portion and a top outside;
    a back portion having a back inside, a back outside and at least one flap opening in folding communication with said folding top;
    a front portion having at least one opening wherein said front portion is in folding communication with said back portion and said folding top covers said front portion when said front portion is in a folded closed position;
    a reagent test sheet in communication with at least a portion of said back portion and interposed between said front portion and said back portion when said front portion is folded over said back portion;
    at least one enclosed bubble containing developer attached to the inside of said flap opening of said back portion, wherein each said enclosed bubble is burst when said folding top is closed and pressure is placed on said folding top; and
    wherein a fecal sample is placed on said reagent test sheet in each said at least one opening of said front portion when said front portion is folded over said back portion, said folding top is folded into a folded closed position and wherein each said at least one enclosed bubble is burst when pressure is placed on said folding top in said folded closed position and said at least one enclosed bubble releases said developer to the fecal sample to indicate the presence of fecal occult blood.

12. A specimen testing device as in claim 11, wherein said raised portion has a pointed tip directly opposing said at least one enclosed bubble containing developer.

13. A specimen testing device as in claim 11, wherein each said at least one enclosed bubble contains a different developer.

14. A specimen testing device as in claim 11, wherein said at least one opening of said front portion is two aligned round openings.

15. A specimen testing device as in claim 11, wherein said at least one opening in said front portion is two aligned round openings and further comprising a hydrophobic barrier between said two aligned round openings.

16. A specimen testing device as in claim 11, wherein said at least one opening of said front portion is three openings forming a triangular shape.

17. A specimen testing device as in claim 11, further comprising a hydrophobic barrier surrounding said at least one flap opening of said back portion.

18. A specimen testing device as in claim 11, further comprising an indicator printed on said reagent test sheet in the center of said at least one opening.

19. A specimen testing device as in claim 11, wherein said at least one enclosed bubble is tear drop shaped.

* * * * *